United States Patent [19]

Burgard et al.

[11] Patent Number: 4,499,057

[45] Date of Patent: Feb. 12, 1985

[54] EXTRACTION OF METALS FROM AQUEOUS SOLUTIONS WITH CYCLIC ORGANIC CARBONATES

[75] Inventors: Michel Burgard, Strasbourg; Marc D. Piteau, Itteville; Alain J. Rollat, Strasbourg Neudorf; Jean-Pierre G. Senet, La Chapelle La Reine, all of France

[73] Assignee: Societe Nationale des Poudres et Explosifs, Paris, France

[21] Appl. No.: 421,723

[22] Filed: Sep. 22, 1982

Related U.S. Application Data

[62] Division of Ser. No. 139,155, Apr. 14, 1980, Pat. No. 4,423,235.

[30] Foreign Application Priority Data

Apr. 13, 1979 [FR] France .................................. 79 09402

[51] Int. Cl.$^3$ .............................................. C01G 43/00
[52] U.S. Cl. ........................................ 423/8; 423/21.5; 423/22; 423/24; 423/54; 423/63; 423/89; 423/100; 423/112; 423/139; 423/181
[58] Field of Search ...................... 423/8, 21.5, 22, 24, 423/54, 63, 89, 100, 112, 139, 181

[56] References Cited

U.S. PATENT DOCUMENTS

| | | | |
|---|---|---|---|
| 2,446,145 | 7/1948 | Strain | 260/340.2 |
| 2,894,816 | 7/1959 | Hyman et al. | 423/22 |
| 2,918,349 | 12/1959 | Seaborg | 423/8 |
| 3,072,613 | 1/1963 | Whelan et al. | 260/340.2 |
| 3,542,841 | 11/1970 | Moore et al. | 260/463 |
| 3,671,563 | 6/1972 | Pfeiffer et al. | 260/340.2 |
| 3,912,801 | 10/1975 | Stephens et al. | 423/8 |
| 4,217,298 | 8/1980 | Shikata et al. | 260/463 |

*Primary Examiner*—Edward A. Miller
*Attorney, Agent, or Firm*—Bucknam and Archer

[57] ABSTRACT

The invention relates to new industrial products of the general formula

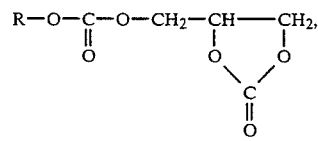

a process for the manufacture of these products and their application as extraction agents in hydrometallurgy.

9 Claims, No Drawings

EXTRACTION OF METALS FROM AQUEOUS SOLUTIONS WITH CYCLIC ORGANIC CARBONATES

This is a division of application Ser. No. 139,155 filed Apr. 14, 1980, now U.S. Pat. No. 4,423,235.

The present invention relates to compounds carrying cyclic carbonate groups, to the processes for the manufacture of these compounds and to their application in hydrometallurgy.

It is known from U.S. Pat. No. 2,446,145 to prepare 2,3-dioxycarbonylpropyl chloroformate by reacting phosgene with glycerol. It is also known, from the same document, to obtain the carbamate and corresponding urethanes by reacting this chloroformate with ammonia or amines.

Furthermore, the value of certain organic substances having the ability wholly or partially to extract metal ions present in aqueous solutions is known. Such ore-leaching solutions, from solutions resulting from attack on recycled scrap metals or, alternatively, from industrial effluents which are harmful to the environment.

Basically, these organic substances, which are referred to as extraction agents, must be capable not only of more or less selectively extracting metal ions from aqueous solutions, but also of returning them to a new, pure and more concentrated aqueous solution which is then treated in a manner which is in itself known.

However, in order to enable all the advantages peculiar to hydrometallurgical techniques to be derived from the extraction agents (versatility, production of metals of high purity, automation, continuous operation and, in particular, utilisation of the ores or waste), the said extraction agents must also possess a number of other properties, namely low solubility in the aqueous phases (a cause of loss), low volatility (also a cause of loss), stability (a further cause of loss), good solubility in inexpensive organic media, good reversibility, high extraction rate, selectivity (in the case of complex solutions), high extraction capacity, high coefficient of extraction, good resistance to recycling, low or zero toxicity and low or zero corrosive character.

In an article appearing in the review HYDROMETALLURGY in 1976, Volume 1, pages 207–240, and entitled "Solvent Extraction of Non-ferrous metals", D. S. FLETT and D. R. SPINK focus on the main extraction agents known and give their spectrum of activity and their conditions of use in each case. A distinction is thus made between solvating, acid, chelating and ionic extraction agents. The solvating extraction agents include phosphates, such as tributyl phosphate (TBP), ketones, such as methyl isobutyl ketone (or MIBK) or isophorone (U.S. Pat. No. 4,008,308), and ethers, such as glycol dibutyl ether (BUTEX). The acid extraction agents include naphthenic and versatic acids and, in particular, di-(2-ethylhexyl)-phosphoric acid (or D2EHPA) (for example U.S. Pat. No. 3,989,607 and French Pat. Nos. 2,342,346 and 2,367,832). The chelating extraction agents essentially include α-hydroxyoximes (commercially known under the name LIX), which are described in U.S. Pat. Nos. 3,224,873 and 3,449,066. Finally, the ionic extraction agents mainly include amines and quaternary ammonium salts, such as those described in French Pat. No. 1,266,363.

The invention itself relates to new chemical compounds which, in their application as extraction agents, do not resemble any known type and thereby have a particular spectrum of application, which is suitable for providing solutions to general or specific problems in the field of extraction.

The carbonates carrying cyclic carbonate groups, according to the invention, have the general formula:

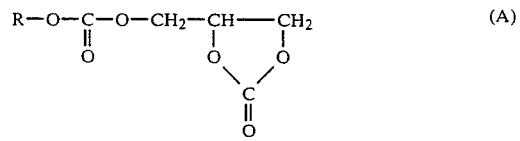

in which R is a linear or branched alkyl group which contains from 1 to 20 carbon atoms and is optionally substituted by one to three groups

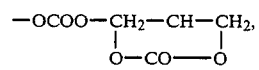

an alicyclic group which contains 4 to 20 carbon atoms and is optionally substituted by one to three groups

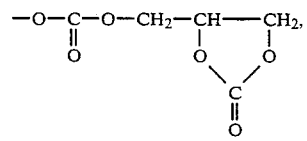

an aralkyl group which contains from 7 to 20 carbon atoms and is optionally substituted by one to three groups

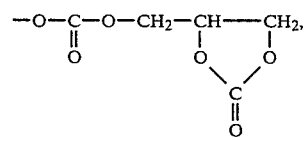

a carboxylate group which contains from 2 to 20 carbon atoms and is optionally substituted by a group

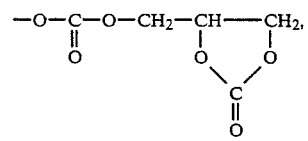

a polyoxyethylene of the formula

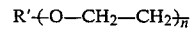

in which n is between 1 and 40 and in which R' is a hydrocarbon group containing from 1 to 10 carbon atoms and optionally carries one or two chains $-(O-CH_2-CH_2)_{n'}$, in which n' is between 1 and 40, which chains are terminated by a group

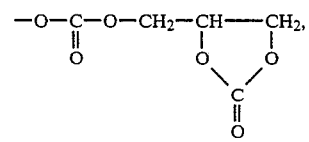

a polyoxypropylene of the formula

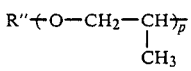

in which p is between 1 and 40 and in which R' is a hydrocarbon group containing from 1 to 10 carbon atoms and optionally carries one or two chains

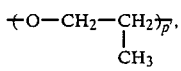

in which p' is between 1 and 40, which chains are terminated by a group

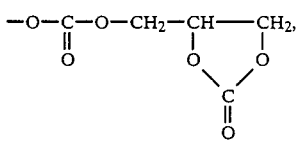

an aryl group containing from 6 to 20 carbon atoms, a polyester of the formula

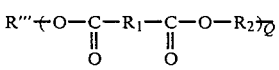

in which Q is between 1 and 20, in which $R_1$ and $R_2$ are identical or different and are a polymethylene chain having from 1 to 8 carbon atoms or a polyether chain having from 1 to 8 carbon atoms, and in which R' is a hydrocarbon group containing from 1 to 10 carbon atoms, or alternatively an aliphatic polycarbonate

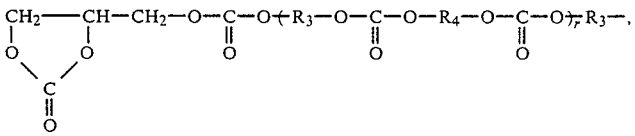

in which r is between 1 and 20 and in which $R_3$ and $R_4$ are identical or different, or in some cases identical and in other cases different, and are polymethylene groups containing from 2 to 8 carbon atoms or polyoxyethylene groups

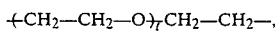

in which t is equal to 1, 2, 3, 4 or 5.

The invention also relates to a process for the manufacture of the new products which have now been described.

The process according to the invention consists in reacting 2,3-dioxycarbonylpropyl chloroformate with an alcohol of the general formula ROH, in which R has one of the meanings given above, OH groups replacing the groups $CO_3$—$CH_2$—($CH$—$CH_2$)$CO_3$ groups where appropriate, at a temperature between −10° and +20° C. and in the presence of an acid acceptor.

According to the invention, the acid acceptor can be an inorganic or organic base. Sodium hydroxide, potassium hydroxide, sodium carbonate, potassium carbonate or sodium bicarbonate can be used as the inorganic base. However, organic bases are preferably used and, amongst these, aliphatic or aromatic tertiary amines are preferred. Pyridine and triethylamine are more particularly preferred, although other amines can be used without exhibiting particular advantages or disadvantages. In the case where R is an aryl group and ROH is a phenolic compound, sodium hydroxide is preferably used as the acceptor, in which case the chloroformate reacts with the phenate RONa.

In contrast to what might be feared in view of the sensitivity of carbonate and cyclic carbonate groups towards bases, no decarbonation or trans-carbonation of the chloroformate used or of the products formed takes place in the course of the reaction, under the precise conditions given above. Furthermore, the yield of the conversion of the alcohol to its carbonate is always high and is generally more than 80% and most frequently more than 85%. Moreover, it is surprising that the yield also remains good when a polyol is used as the starting reactant.

In principle, a solvent is used as the reaction medium, but, because the product formed itself constitutes an excellent solvent for the reactants, the process does not therefore necessarily require the presence of a solvent. Suitable solvents which may be mentioned are organic solvents for the alcohols and polyols in question and for the 2,3-dioxycarbonylpropyl chloroformate, which solvents are inert towards these reactants and also towards the acid acceptor. Examples which may be mentioned are aliphatic and aromatic hydrocarbons, halogenated hydrocarbons, ethers, ketones and esters, such as hexane, benzene, toluene, xylene, carbon tetrachloride, chloroform, methylene chloride, tetrahydrofurane, glymes, acetone, cyclohexanone and ethyl acetate.

The proportions of reactants to be used are those corresponding to the stoichiometry of the reaction, that is to say that at least one mol of chloroformate is reacted per mol of hydroxyl carried by the alcohol, in the presence of an equimolecular amount of acid acceptor. It is preferred to use a slight excess of chloroformate, preferably from 5 mol % to 15 mol %, and a corresponding excess of acid acceptor.

When the reaction has ended, which requires from 0.5 to 5 hours, the reaction medium is advantageously washed with acidified water and then with pure water, after which the said mixture is dried over a dehydrating salt, such as an alkali metal sulphate or alkaline earth metal sulphate, and the solvent is evaporated off; in the majority of cases, the resulting product does not require any purification treatment.

The invention also relates to a process for the separation, by liquid-liquid extraction, of valuable metal species from an aqueous solution in which they are present, characterised in that (1) the said aqueous solutions are brought into contact with an organic phase comprising a compound of the general formula:

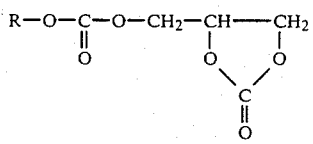

(A)

optionally dissolved in an essentially water-immiscible organic solvent, with the result that the said valuable metal species are at least partially extracted into the organic phase, (2) the charged organic phase containing the valuable metal species extracted from the aqueous solution in the form of a complex with the compound of the general formula (A) is separated off, and (3) the valuable metal species are recovered from the organic phase by bringing the latter into contact with an aqueous stripping medium.

The valuable metal species with which the invention is especially concerned are the following metal ions in particular: Zn(II), Cd(II), Hg(II), Fe(III), Co(II), Cu(I), Rh(III), Cu(II), Pd(II), Pt(II), Mo(V), V(IV), Pb(II), Ag(I), Au(III) and Ga(III), and also Na(I), K(I), Hg(I), U(IV), U(VI) and the lanthanides in oxidation states (II), (III) or (IV).

Conventional problems which arise but which can be solved by using the compounds of the general formula (A) are, for example, the extraction of cobalt in the presence of nickel, the extraction of zinc in the presence of nickel, the extraction of molybdenum in the presence of uranium and strontium, and the extraction of gold in the presence of metals from platinum mines.

The counter-ions which can be found in the aqueous solutions to which the invention relates are essentially $NO_3^-$, $Cl^-$, $ClO_4^-$, $SO_4^=$ and $SCN^-$, the latter being preferred in the majority of cases except in the case of gold, for which a $Cl^-/NO_3^-$ medium is particularly suitable.

The essentially water-immiscible organic solvents which are preferably associated with the compounds according to the invention, in the organic extraction phase, are mainly aliphatic hydrocarbons, aromatic hydrocarbons and chlorinated aliphatic hydrocarbons, such as, for example, paraffin oils, benzene, toluene, xylene, dichloroethane, chloroform and, in general terms, organic solvents having a flash point above 65° C.

The range of pH values which can be used in the aqueous phase charged with the valuable metal species to be extracted, and in the stripping medium, is between −1 and 12, preferably between 0 and 10, and this is no different from the pH conditions normally encountered in the processes of the prior art. It is specified that the term stripping is to be understood as meaning the transfer of at least part of the metal or metals present in the organic phase into an aqueous medium, referred to as the "stripping medium", which can be subjected in a manner which is in itself known to a subsequent treatment for recovering the said metals, the latter thus being obtained in a very pure state. Of course, each starting aqueous solution containing metal is subject to its own optimum conditions, as will be understood preferably well by those skilled in the art.

Although the compounds according to the invention can form the organic extraction phase by themselves, it generally suffices to use dilute solutions thereof in an organic solvent of a very general type defined above. However, it is possible to use concentrated solutions of the order of 50 to 75% strength by weight of the purpose of facilitating transportation and handling, and to carry out possible subsequent dilutions, at the time of use, in order to obtain solutions containing at least 1%, preferably at least 5 to 10%, by weight, relative to the solvent, of extraction agent according to the invention.

Amongst the compounds of the general formula (A), according to the invention, some are particularly preferred in their application to the liquid-liquid extraction of valuable metal species.

For the purpose of extracting gold from aqueous solutions in which it is present, it is advantageous to use, in particular, alkyl 2,3-dioxycarbonylpropyl carbonates in which alkyl is methyl, n-propyl, n-butyl, n-pentyl, n-hexyl, n-heptyl, n-octyl and their higher linear homologues up to octadecyl, and also glycol 2,3-dioxycarbonylpropyl carbonate or hexane-1,6-diol 2,3-dioxycarbonylpropyl carbonate, benzyl 2,3-dioxycarbonylpropyl carbonate, phenyl 2,3-dioxycarbonylpropyl carbonate, tri-, tetra-, penta-, hexa- or hepta-(ethlene glycol)2,3-dioxycarbonylpropyl carbonate, trimethylolpropane tri(2,3-dioxycarbonylpropyl)carbonate poly-[(diethylene glycol)carbonate]di2,3-dioxycarbonylpropyl carbonates in which the polycarbonate part has a mass of less than 3,000, and poly-(butanediol carbonate)di2,3-dioxycarbonylpropyl carbonates in which the polycarbonate part has a mass of less than 2,000, and also in which the polycarbonate part may or may not be in the form of a block copolymer.

For the purpose of extracting zinc, molybdenum and cobalt, and metals other than gold and other than metals from platinum mines, it is advantageous to use the polyethylenes of the formula

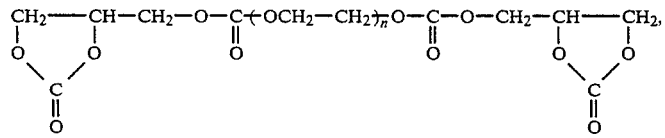

in which n is equal to or greater than 2 and of which the molecular weight preferably does not exceed 5,000, and, to a lesser extent, the diol and triol 2,3-dioxycarbonylpropyl carbonates obtained by condensing propylene oxide with aliphatic diols or triols containing from 2 to 8 carbon atoms, and preferably having an overall mass of less than 3,000.

It will be appreciated that, apart from their ability to extract valuable metal species from aqueous solutions in which they are present, the compounds according to the invention have physical and chemical properties which make them extremely attractive. In fact, they are sparingly soluble or insoluble in water, and vice versa. In contrast, they are very soluble in the solvents commonly used in hydrometallurgy and have a density which is generally of the order of 1.4 tonnes/m³, this being substantially greater than the density of the aqueous solutions charged with valuable metal species. Their volatility and their toxicity are very low. On the other hand, by virtue of the presence of the carbonate groups, they are very capable of withstanding the high mechanical stresses to which extraction agents are subjected, and they therefore have a very satisfactory suitability for recycling. Finally, neither the compounds themselves nor the products which could result from their accidental decomposition can exert a corrosive action on industrial equipment.

These properties give the compounds according to the invention a considerable advantage, in particular over ethylene carbonate and propylene carbonate, which are known as extractants from U.S. Pat. No. 3,912,801 but are not easily used to good effect in industry because of their solubility in water, their low molecular weight and their relative instability under basic conditions.

Further advantages of the products and of the process according to the invention will become apparent in the following examples, which are given only to illustrate the invention and consequently cannot limit the latter.

EXAMPLE 1

Preparation of 2,3-dioxycarbonylpropyl chloroformate 500 ml of liquid phosgene are introduced into a reactor equipped with a 40° C. reflux condenser, a thermometer, a stirrer and a dropping funnel.

276 g (3 mols) of glycerol are run in slowly in the course of about 3 hours, whilst keeping the temperature between 0° and +5° C.

The mixture is stirred for 1 hour at 0° C. and is then left to return to ambient temperature in the course of 2 hours.

A stream of nitrogen is passed through until the excess phosgene has been completely removed, 400 ml of methylene chloride are added and the mixture is washed 3 times with 500 ml of iced water.

The organic phase is collected and dried over sodium sulphate. After evaporating off the solvent under reduced pressure at 30° C., 348 g of product are obtained, this being a yield of 64% relative to the glycerol.

Analysis: Hydrolysable chlorine level: 20.2% (theory 19.56%). Infra-red spectrum absorption bands: $\nu > C = 0$ (chloroformate) at 1,780 cm$^{-1}$ and $\nu > C = 0$ (cyclic carbonate) at 1,800 cm$^{-1}$

EXAMPLE 2

Preparation of 2,3-dioxycarbonylpropyl-octyl carbonate 346 g (1.9 mols) of the chloroformate prepared above, 247 g (1.9 mols) of n-octanol and 600 ml of methylene chloride are introduced into a reactor equipped with a reflux condenser, a thermometer, a stirrer and a dropping funnel.

152 g (2.2 mols) of pyridine (that is to say a molar excess of 15%) are run in over a period of about 1 hours, whilst keeping the temperature between −5° and 5° C.

The mixture is stirred for 1 hour at 0° C. and is then left to return to ambient temperature in the course of about 2 hours.

The pyridine hydrochloride is removed by filtration and the organic phase is washed with twice 500 ml of water.

After drying over magnesium sulphate and removing the solvent by evaporation under reduced pressure, the product is topped at 100° C. under a pressure of 1 mm Hg for 30 minutes.

460 g of a colourless oil, which crystallises at ambient temperature, are thus obtained. The yield is 88% relative to the chloroformate.

Analyses: Infra-red spectrum: absorption bands $\nu C = 0$ (linear carbonate) at 1,740 cm$^{-1}$ and $\nu C = 0$ (cyclic carbonate) at 1,800 cm$^{-1}$. NMR spectrum agrees with the formula.

It should be noted that more volatile or less volatile alkyl carbonates can be synthesised with the same ease, under the same conditions and with a comparable success to that which has just been reported.

EXAMPLE 3

Synthesis of trimethylolpropane tri-(2,3-dioxycarbonylpropyl carbonate).

93.8 g (0.7 mol) of trimethylolpropane, 400 cm$^3$ of acetone and 183 g (2.31 mols) of pyridine are introduced into a 2 liter reactor. The temperature is kept at about 0° C. and a solution of 417 g (2.31 mols) of 2,3-dioxycarbonylproyl chloroformate in 400 cm$^3$ of acetone is added. After stirring for two hours at ambient temperature, the reaction mixture is filtered, the filtrate is concentrated under reduced pressure, the residue is taken up in 1.5 liters of methylene chloride and the solution is washed with acidified water and then with pure water. The organic solution is dried, filtered and concentrated under reduced pressure. 347 g (yield 88%) of trimethylolpropane tri-(2,3-dioxycarbonylpropyl carbonate) are thus obtained.

Melting point: 120° C. Residual OH level: 0%
Infra-red spectrum:

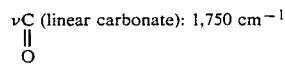

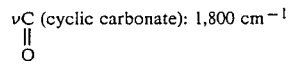

This spectrum is in total agreement with theory.

EXAMPLE 4

Synthesis of tetraethylene glycol di-(2,3-dioxycarbonylpropyl carbonate).

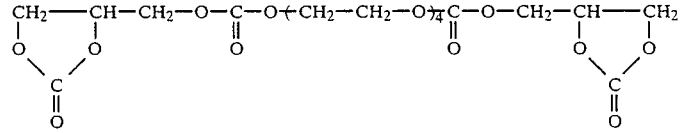

2.888 kg (16 mols) of 2,3-dioxycarbonylpropyl chloroformate and 5 liters of anhydrous methylene chloride are introduced into a 20 liter glass reactor.

The temperature is kept between −4° and +2° C. and a mixture of 1.552 kg (8 mols) of tetraethylene glycol, 1.430 kg (18.1 mols) of pyridine (that is to say an excess of 13% relative to stoichiometry) and 1 liter of anhydrous methylene chloride is run in slowly, whilst stirring.

After the introduction, which takes 1 hour 45 minutes, the reaction mixture is heated to between +15° and +18° C. and this temperature is maintained for one hour.

7 liters of salt water are added and the organic phase is separated off. The latter is washed three times with a mixture of 7 liters of salt water and 500 ml of concentrated hydrochloric acid, twice with 7 liters of salt water and once with 7 liters of demineralised water.

The organic phase is dried over anhydrous sodium sulphate and the solvent is removed by evaporation under reduced pressure at 50° C.

3.225 kg (yield 83.6%) of a very viscous product are thus collected, the main characteristics of this product being as follows:
  water content: 0.040%
  content of residual OH groups $\leq 10^{-2}$ eq/kg
  Tetraethylene glycol di-(2,3-dioxycarbonylpropyl carbonate)

$$CH_2\text{---}CH\text{---}CH_2\text{---}O\text{---}\underset{\underset{O}{\|}}{C}\text{---}O(CH_2\text{---}CH_2\text{---}O)_{\overline{74}}\underset{\underset{O}{\|}}{C}\text{---}O\text{---}CH_2\text{---}CH\text{---}CH_2$$
$$\underset{\underset{\diagdown C \diagup}{\underset{\|}{O}}}{O\quad\quad O}\quad\quad\quad\quad\quad\quad\quad\quad\quad\quad\quad\quad\quad\quad\quad\quad\quad\quad\underset{\underset{\diagdown C \diagup}{\underset{\|}{O}}}{O\quad\quad O}$$

Viscous liquid, slightly amber-coloured, possessing a slight odour:
  Melting point: 14° C. (transition point)
  Vapour pressure at 20° C.: 5 mm Hg; at 100° C.: 22 mm Hg
  Density $d_{25}^{25}$: 1.41
  Viscosity at 25° C.: 60,000 cP
  Refractive index at 25° C., $n_D^{25}$: 1.4750
  Solubility: insoluble in water, good solubility in organic solvents (60 g in 100 g of $CH_2Cl_2$ at 20° C.)

EXAMPLE 5

Synthesis of poly-(ethyleneglycol) di-(2,3-dioxycarbonylpropyl carbonate)

$$CH_2\text{---}CH\text{---}CH_2\text{---}O\text{---}\underset{\underset{O}{\|}}{C}\text{---}O(CH_2\text{---}CH_2\text{---}O)_{\overline{n}}\underset{\underset{O}{\|}}{C}\text{---}O\text{---}CH_2\text{---}CH\text{---}CH_2$$
$$\underset{\underset{\diagdown C \diagup}{\underset{\|}{O}}}{O\quad\quad O}\quad\quad\quad\quad\quad\quad\quad\quad\quad\quad\quad\quad\quad\quad\quad\quad\quad\quad\underset{\underset{\diagdown C \diagup}{\underset{\|}{O}}}{O\quad\quad O}$$

n = 13

300 g (0.5 mol) of polyethylene glycol (Mn=600), 300 ml of anhydrous methylene chloride and 87 g (1.1 mols) of pyridine are introduced into a 2 liter reactor.

The temperature is kept between 0° and +5° C. and a solution of 198.5 g (1.1 mols) of 2,3-dioxycarbonylpropyl chloroformate in 300 ml of methylene chloride is added dropwise, whilst stirring.

After stirring for two hours at ambient temperature, the reaction mixture is filtered and the resulting filtrate is washed with an aqueous solution of hydrochloric acid and then with distilled water until the wash waters are neutral.

The organic phase is dried over magnesium sulphate and the solvent is removed by evaporation under reduced pressure.

366.7 g (yield 82.6%) of product are thus obtained and the infra-red spectrum of this product is correct.
  Content of residual OH groups: 0.01 eq/kg
  Total chlorine content $\leq 400$ ppm
  Mn=890
  Soluble in: acetone, chloroform, ether, toluene and benzene.

EXAMPLE 6

Synthesis of poly-[(diethylene glycol carbonate)]di-(2,3-dioxycarbonylpropyl carbonate)

$$CH_2\text{---}CH\text{---}CH_2O\text{---}\underset{\underset{O}{\|}}{C}\text{---}O(CH_2\text{---}CH_2\text{---}O\text{---}CH_2\text{---}CH_2\text{---}O\text{---}\underset{\underset{O}{\|}}{C}\text{---}O)_{\overline{m}}CH_2\text{---}CH\text{---}CH_2$$
$$\underset{\underset{\diagdown C \diagup}{\underset{\|}{O}}}{O\quad\quad O}\quad\quad\quad\quad\quad\quad\quad\quad\quad\quad\quad\quad\quad\quad\quad\quad\quad\quad\quad\quad\quad\quad\underset{\underset{\diagdown C \diagup}{\underset{\|}{O}}}{O\quad\quad O}$$

m ≃ 10

The procedure used is strictly identical to the above procedure (Example 5), using 410 g (0.33 mol) of poly-(diethylene glycol carbonate), 58 g (0.73 mol) of pyridine (that is to say an excess of 10% relative to stoichiometry), 600 ml of anhydrous methylene chloride and 132 g (0.73 mol) of 2,3-dioxycarbonylpropyl chloroformate.

435 g of product are thus collected, the infra-red spectrum of this product agrees with the formula given above and its number-average molecular weight is about 1,500, its content of OH groups is less than or equal to 0.02 eq/kg and the total chlorine level is 0.06%.

EXAMPLE 7

Synthesis of 2,3-dioxycarbonylpropyl (ethyl methacrylate) carbonate 11.4 g (0.1 mol) of 2-hydroxyethyl methacrylate, 9 g (0.11 mol) of pyridine and 50 ml of 2,3-dioxycarbonylpropyl chloroformate in 30 cm³ of methylene chloride are placed in a 250 ml reactor in the absence of moisture. Stirring is continued for a further one hour at ambient temperature and 50 cm³ of acidified water are then added.

The organic phase is decanted, dried and evaporated under reduced pressure. 23 g (yield: 84%) of the mixed carbonate of 2,3-dioxycarbonylpropyl and of ethyl methacrylate are thus obtained.

Infra-red spectrum:
$\nu C=O$ (cyclic carbonate): 1,830 cm$^{-1}$
$\nu C=O$ (linear carbonate): 1,755 cm$^{-1}$
$\nu C=O$ (ester): 1,720 cm$^{-1}$
$\nu C=C$: 1,630 cm$^{-1}$ Nuclear magnetic resonance spectrum:

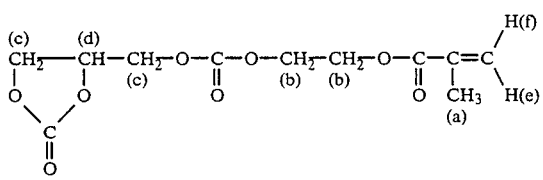

(a) hump at 1.98 ppm, 3 H
(b) singlet at 4.38 ppm
(c) complex hump from 4.1 to 4.75 ppm  } 9H
(d) hump from 4.7 to 5.1 ppm
(e) hump at 5.6 ppm, 1 H
(f) hump at 6.13 ppm, 1 H

EXAMPLES 8 TO 13

Extraction of Gold

A solution of gold was prepared under the same conditions as those usually encountered in the case of solutions resulting from the leaching of auriferous ores. This solution contained 100 ppm of Au in the form of NaAuCl$_4$, with NaCl (2M) as the base salt. Its pH was equal to 1.7.

One volume of this aqueous solution was mixed with one volume of a molar solution of compounds according to the invention in various solvents. After stirring the two phases, the percentage of gold extracted from the aqueous phase and present in the organic phase was measured. The results are summarised in Table 1 below:

TABLE 1

| Example | Extractant | Solvent | % of gold extracted |
|---|---|---|---|
| 8 | Compound of Example 2 | Benzene | 41 |
| 9 | Compound of Example 2 | Chloroform | 40 |
| 10 | Compound of Example 4 (1) | Dichloroethane | 100 |
| 11 | Compound of Example 4 (1) | Chloroform | 100 |
| 12 | Compound of Example 5 | Chloroform | 100 |

(1) but with 3 ether bridges instead of 4.

By way of comparison (Example 13), methyl isobutyl ketone also makes it possible to achieve total extraction of the gold, but only provided that it is used pure and not diluted in a solvent. Furthermore, it is a relatively volatile compound which is slightly soluble in water and has a lower density than that of water.

EXAMPLES 14 TO 17

Extraction of gold in the presence of platinum

An attempt was made selectively to extract gold from an aqueous phase containing both gold (in the form of NaAuCl$_4$, as in the preceding example) and platinum in solution, in an amount of 0.5 g/liter in the case of Au and 2.5 g/liter in the case of Pt. The solution contained sodium chloride as the base salt (3M) and was acidified with hydrochloric acid (1N). The results obtained are grouped in Table 2:

TABLE 2

| | | Au | | Pt | |
|---|---|---|---|---|---|
| Example | Extractant | Organic phase (g/liter) | Aqueous phase (g/liter) | Organic phase (g/liter) | Aqueous phase (g/liter) |
| 14 | Butex (1) | 0.465 | 0.035 | 0 | 2.5 |
| 15 | Compound of Example 5 (2) | 0.500 | 0.000 | 0.05 | 2.45 |
| 16 | Compound of Example 5 (3) | 0.370 | 0.130 | 0 | 2.5 |
| 17 | Compound of Example 4 | 0.390 | 0.110 | 0 | 2.5 |

(1) Butex, which has the formula BuOCH$_2$CH$_2$OCH$_2$CH$_2$OBu, is a known extractant. It was employed here in the pure state.
(2) In solution at a concentration of 445 g/liter (0.5 M) in chloroform
(3) In solution at a concentration of 44.5 g./liter (0.05 M) in chloroform
(4) In solution at a concentration of 200 g/liter (0.4 M) in chloroform It is seen that the compounds according to the invention possess the same properties (selectivity and capacity) as Butex, but that they can be used in diluted form whereas Butex must be used in the pure form.

EXAMPLE 18

Extraction of gold in a simulator

The compound of Example 4, in a 0.2M solution in chloroform, was used to extract the gold which was present, in the dissolved state, in an amount of 1,000 ppm, in an aqueous phase containing sodium chloride as the base salt (2M) and acidified with hydrochloric acid (0.443N from the start).

These phases were subjected to the conditions of AKUFVE 110 (intimate mixing, centrifugation of the phases and continuous extraction) for 4 hours, whilst varying the concentration of H$^+$.

$$\text{The ratio } D = \frac{\text{concentration of Au in the organic phase}}{\text{concentration of Au in the aqueous phase}}$$

was measured as a function of the concentration of H$^+$. The results are reported in Table 3.

TABLE 3

| D | 0.70 | 0.72 | 0.73 | 0.75 | 0.77 | 0.82 | 0.93 | 1.09 | 1.27 | 1.65 |
|---|---|---|---|---|---|---|---|---|---|---|
| (H$^+$) (mols/liter) | 0.5 | 0.75 | 1.0 | 1.25 | 1.50 | 1.75 | 2.00 | 2.25 | 2.5 | 2.75 |

No deterioration of the extraction agent was observed at the end of the experiment.

The gold metal was recovered by aqueous stripping using oxalic acid in accordance with the method described by B. F. Rimmer, Chemistry and Industry, pages 63–66, of Jan. 19, 1974. The equation is:

$$3(COOH)_2 + 2HAuCl_4 \rightarrow 2Au + 6CO_2 + 8HCl$$

Furthermore, under the same conditions, it was possible to establish that Rh(III) was not extracted by the tetraethylene glycol di-(2,3-dioxycarbonylpropyl carbonate) used.

Finally, it should be noted that the extraction of gold can also be carried out, using this compound, in the presence of nitrate anions in addition to the chloride anions.

EXAMPLES 19 TO 25

Separation of uranium, molybdenum and strontium

An attempt was made to solve the problem of separating Mo(V) from an aqueous solution also containing U(VI) and $Sr^{2+}$.

Tetraethylene glycol di-(2,3-dioxycarbonylpropyl carbonate) was used as the extraction agent, in solution in dichloroethane, and the aqueous phase also contained ammonium thiocyanate (2M).

Initially, an attempt was made to extract molybdenum on its own, varying the concentration thereof, and also the pH and the concentration of ascorbic acid, in the aqueous phase (compare Table 4):

TABLE 4

| Example | [Mo] ppm | $(H^+)$ | (Ascorbic acid) |
|---|---|---|---|
| 19 | 500 | $10^{-1}$ | 25 g/l |
| 20 | 250 | $5.10^{-2}$ | 12.50 g/l |
| 21 | 100 | $2.10^{-2}$ | 5 g/l |

Under these conditions (the ascorbic acid is intended to reduce Mo(VI) to Mo(V)), the extractions reported in Table 5 were obtained:

TABLE 5

| Concentration of extractant (g/liter) | 0 | 20 | 30 | 60 | 100 | 150 | 200 |
|---|---|---|---|---|---|---|---|
| % of Mo extracted in Example 19 | 0 | 12 | 16 | 18 | 21 | 32 | 40 |
| % of Mo extracted in Example 20 | 0 | 5.2 | 5.6 | 9.7 | 15.4 | 32.6 | 56.2 |
| % of Mo extracted in Example 21 | 0 | 4.7 | 8.4 | 10.3 | 19.2 | 42.5 | 54.7 |

With the concentration of $H^+$ then fixed at $2 \cdot 10^{-2}M$ and the concentration of thiocyanate fixed at 2M, the percentage of Mo, Sr, U(VI) and again U(VI) extracted from an aqueous solution containing 100 ppm of Mo and 100 ppm of U (Example 22), 100 ppm of Sr (Example 23), 100 ppm of U (Example 24) and 100 ppm of Mo and 100 ppm of U (Example 25), respectively, were measured in Examples 22 to 25. The results obtained as a function of the concentration of the same extractant as in Examples 19 to 21, in dichloroethane, are reported in Table 6:

TABLE 6

| Concentration of extractant (g/liter) | 0 | 20 | 30 | 60 | 100 | 150 | 200 |
|---|---|---|---|---|---|---|---|
| % of Mo extracted (Example 22) | 0 | 5.6 | 4.7 | 12.6 | 30.4 | 43.5 | 40.2 |
| % of Sr extracted (Example 23) | 1 | 1 | 1 | 1 | 1 | 1 | 1 |
| % of U(VI) extracted (Example 24) | 0 | 0 | 0 | 0 | 1 | 2 | 40.7 |
| % of U(VI) extracted (Example 25) | 0 | 0 | 0 | 0 | 1 | 3.7 | 44.4 |

These results show that it is possible very satisfactorily to extract Mo and then U(VI) without extracting Sr.

EXAMPLE 26

Selective extraction of Co in the presence of Ni

Solutions of tetraethylene glycol di-(2,3-dioxycarbonylpropyl carbonate) in chloroform were used for the purpose of extracting the cobalt which was present, in an amount of 200 ppm, in an aqueous solution of pH=2, additionally containing one mol per liter of potassium thiocyanate and 200 ppm of $Ni^{++}$.

The results obtained as a function of the concentration of extractant in mols/liter are reported in Table 7:

TABLE 7

| Concentration of extractant (mols/liter) | 0.127 | 0.204 | 0.233 | 0.271 | 0.311 | 0.498 |
|---|---|---|---|---|---|---|
| % of Co extracted | 0 | 7 | 13 | 25 | 39 | 90 |
| % of Ni extracted | 0 | 0 | 0 | 0 | 0 | 0 |

These results show that, using the compounds according to the invention, it is possible to separate cobalt from the nickel with which it is frequently associated.

EXAMPLE 27

Comparison with commercial products

The compounds according to the invention, of the formula $$CH_2\!-\!\!\!-\!CH\!-\!CH_2\!-\!O\!-\!\overset{O}{\underset{\|}{C}}\!-\!O\!\!\left(CH_2\!-\!CH_2\!-\!O\right)_{\!13}\!\overset{O}{\underset{\|}{C}}\!-\!O\!-\!CH_2\!-\!CH\!-\!\!\!-\!CH_2$$

$$\underset{O\diagdown\;\diagup O}{\phantom{XX}}\underset{\underset{O}{\overset{\|}{C}}}{\phantom{XX}}\underset{\phantom{XX}}{\phantom{XX}}\underset{O\diagdown\;\diagup O}{\phantom{XX}}\underset{\underset{O}{\overset{\|}{C}}}{\phantom{XX}}$$

having a mass of 890, was compared with a polyethylene glycol $HO\text{-}(CH_2CH_2O)_{20}H$ (mass: 1,000) and with Brij 35 of the formula $C_{12}H_{25}O\text{-}(CH_2CH_2O)_n H$ (in which n=23 and which has a mass of 1,200).

For this purpose, solutions containing 10 g/liter of these extractants in dichloroethane were prepared, the aqueous phase being two molar in respect of $NH_4SCN$ and having a pH adjusted to 1 with hydrochloric acid.

The extraction achieved by mixing the organic and aqueous phases thus obtained was measured, the aqueous phase containing 100 ppm of the various metals tested (10 ppm in the case of Hg). The percentage extractions are indicated in Table 8:

TABLE 8

| Extractant | Zn(II) | Mo(V) | Co(II) | FE(III) | Hg(II) | V(IV) | Cu(I) | Pb(II) | Cd(II) |
|---|---|---|---|---|---|---|---|---|---|
| Compound B | 99 | 98 | 95.2 | 80 | 26 | 20 | 31.2 | 2.4 | 4.8 |
| PEG 1,000 | 99 | 91 | 87 | 34 | 11 | 8 | 7 | 2 | 3 |

TABLE 8-continued

| Extractant ↓ | Zn(II) | Mo(V) | Co(II) | FE(III) | Hg(II) | V(IV) | Cu(I) | Pb(II) | Cd(II) |
|---|---|---|---|---|---|---|---|---|---|
| Brij 35 | 100 | 99 | 99 | 92 | 56 | 75 | 38 | 12 | — |

It is seen that the compound according to the invention has a comparable extraction capacity to that of commercial products, even though it possesses a substantially smaller mass and number of ether bridges. This therefore shows the extremely favourable effect of combining the cyclic carbonate group with a polyether chain.

It was also noted that the compound B is capable of extracting praseodymium (4%), to a small extent but very selectively, under the above conditions.

Finally, since compound B extracts Zn but not Ni, it makes it possible to separate these metals without resorting to the use of phosphonic acid as in the process described in French Pat. No. 2,367,832.

example comprised between 1 and 5, without disadvantages. The reaction of extraction being for example:

In order to demonstrate that the compounds according to the invention can, in particular, extract valuable metal species by this mechanism, which is referred to as the mechanism of extraction by alkali metal complexation, aqueous solutions of potassium thiocyanate (M) in a medium of pH 2 were first prepared, the concentration of the extractant in dichloroethane being varied (Table 9).

TABLE 9

| | EXTRACTANTS | | | | | | | |
|---|---|---|---|---|---|---|---|---|
| BUTEX (Example 28) | | DEBCY (Example 29) (1) | | TEBCY (Example 30) (2) | | QEBCY (Example 31) (3) | |
| [EXTR.] mols/liter | [K+] $10^{-3}$ mols/liter | [EXTR.] mols/liter | [K+] $10^{-3}$ mols/liter | [EXTR.] mols/liter | [K+] $10^{-3}$ mols/liter | [EXTR.] mols/liter | [K+] $10^{-3}$ mols/liter |
| | | | | | | 0.10 | 0.4 |
| | | | | | | 0.20 | 1.0 |
| | | 0.35 | 0.3 | 0.30 | 0.6 | 0.30 | 2.2 |
| 0.45 | 0.35 | 0.40 | 0.4 | 0.40 | 1.0 | 0.40 | 3.7 |
| 0.50 | 0.40 | 0.50 | 0.7 | 0.50 | 1.9 | 0.50 | 6.8 |
| 0.60 | 0.40 | 0.60 | 1.0 | 0.60 | 2.3 | 0.55 | 8.5 |
| 0.70 | 0.45 | 0.70 | 1.4 | 0.70 | 3.7 | | |
| 0.80 | 0.50 | 0.80 | 2.0 | 0.80 | 5.1 | | |
| 0.90 | 0.55 | 0.90 | 2.6 | | | | |
| 1.00 | 0.6 | 1.00 | 3.7 | | | | |

EXAMPLES 28 TO 37

It was desired to investigate the type of mechanism by which the compounds according to the invention behaved as extractants. It is known, for example, that compounds of the polyether type, such as the above-mentioned Butex, extract valuable metal species by solvation coupled with protonation of the said extractant in a strongly acid medium:

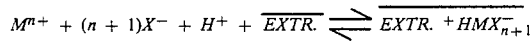

(in which M is the metal, n is its valency, $X^-$ is the anion of the base salt and EXTR. is the extractant). In a mechanism of this kind, the pH obviously has a great influence and must generally be less than or equal to zero.

If the latter condition seems prohibitive, it is possible to extract via an actual solvation mechanism:

In this case, the extractant only partially complexes the metal and its activity depends substantially on the base salt, which constitutes a further constraint. In contrast, with the compounds according to the invention, the nature of the cation $M_s^+$ of the base salt is very important, while the pH of the solution can be positive, for (1) Diethylene glycol 2,3-dioxycarbonylpropyl carbonate
(2) Triethylene glycol 2,3-dioxycarbonylpropyl carbonate
(3) Tetraethylene glycol di-2,3-dioxycarbonylpropyl carbonate.

This table shows that BUTEX extracts virtually no potassium, compared with DEBCY, which contains the same number of ether bridges, and a fortiori compared with TEBCY and QEBCY.

This observation having been made, the influence of the nature of the associated alkali metal cation on the extraction of 100 ppm of $Co^{2+}$, added to the above aqueous solution (molar in terms of base salt, pH=2), was studied.

Tables 10 and 11 report the results obtained with triethylene glycol di-2,3-dioxycarbonylpropyl carbonate and tetraethylene glycol di-2,3-dioxycarbonylpropyl carbonate respectively.

TABLE 10

| EXAMPLE | (Extractant) (mols/liter) | 0.12 | 0.18 | 0.3 | 0.36 | 0.48 | 0.60 |
|---|---|---|---|---|---|---|---|
| 32 | % of $Co^{2+}$ extracted (NaSCN) | 0 | 0 | 0 | 0 | 1 | 10 |
| 33 | % of $Co^{2+}$ extracted (NH4SCN) | 0 | 0 | 2 | 6 | 15 | 30 |
| 34 | % of $Co^{2+}$ extracted (KSCN) | 2 | 4 | 14 | 25 | 55 | 77 |

TABLE 11

| EXAMPLE | (Extractant) (mols/liter) | 0.12 | 0.18 | 0.3 | 0.36 | 0.48 | 0.60 |
|---|---|---|---|---|---|---|---|
| 35 | % of $Co^{2+}$ extracted (NaSCN) | 0 | 0 | 4 | 9 | 23 | 34 |
| 36 | % of $Co^{2+}$ extracted (NH$_4$SCN) | 5 | 11 | 30 | 49 | 77 | 92 |
| 37 | % of $Co^{2+}$ extracted (KSCN) | 17 | 46 | 85 | 92 | 96 | 99 |

This shows the extremely favourable influence of the presence of the $K^+$ cation in the aqueous phase, with respect to the extraction of $Co^{2+}$. This effect is found regardless of the anion associated with $K^+$ in the base salt, with the result that the extraction can be carried out with excellent results, at a very moderate pH, with an inexpensive base salt such as KCl. This is particularly advantageous for the treatment of slightly acid waste waters in which the valuable metal species are in a highly dilute form.

EXAMPLE 38

Synthesis of phenyl 2,3-dioxycarbonylpropyl carbonate 51.7 g (0.55 mol) of phenol, 41.5 g (0.52 mol) of pyridine and 300 cm³ of chloroform are placed in a 500 cm³ reactor. 90.3 g (0.5 mol) of 2,3-dioxycarbonylpropyl chloroformate, diluted in 50 cm³ of chloroform, are added to this solution, kept at 0° C. The reaction mixture is stirred for 2 hours at ambient temperature and then washed with 200 cm³ of acidified water, 200 cm³ of pure water, 200 cm³ of carbonated water and finally 200 cm³ of pure water. After drying, the organic phase is evaporated under reduced pressure. 80.7 g (yield: 71.5%) of phenyl 2,3-dioxycarbonylpropyl carbonate, which melts at 94° C., are thus obtained.

IR spectrum:

$\diagdown$C=O linear 1,750 cm$^{-1}$ $\diagdown$C=O cyclic 1,800 cm$^{-1}$ $\diagdown$C=C$\diagup$ aromatic 1,590 cm$^{-1}$ NMR spectrum:

(a) hump centred at 4.63 ppm (4H)
(b) hump centred at 5.25 ppm (1H)
(c) hump centred at 7.35 ppm (5H)

EXAMPLE 39

Methyl 2,3-dioxycarbonylpropyl carbonate 21.1 g (0.66 mol) of methanol, 49.8 g (0.63 mol) of pyridine and 300 cm³ of chloroform are placed in a 500 cm³ reactor. With the temperature at 0° C., 108.2 g (0.60 mol) of 2,3-dioxycarbonylpropyl chloroformate, diluted in 50 cm³ of chloroform, are added. The reaction mixture is stirred for 2 hours at ambient temperature and subsequently washed with acidified water and then with pure water.

After drying, the organic phase is concentrated under reduced pressure. 42.8 g, that is to say a yield of 40%, of methyl 2,3-dioxycarbonylpropyl carbonate, which melts at 90° C., are thus obtained.

IR spectrum:

$\diagdown$C=O cyclic: 1,800 cm$^{-1}$ $\diagdown$C=O linear: 1,740 cm$^{-1}$

NMR spectrum:

(a) singlet at 3.75 ppm (3H)
(b) hump centred at 4.45 ppm (4H)
(c) hump centred at 5.10 ppm (1H)

We claim:

1. Process for the separation, by liquid-liquid extraction, of valuable metal species from an aqueous solution in which they are present, comprising:

(1) bringing the said aqueous solution into contact with an organic phase comprising a compound which is a carbonate having cyclic carbonate groups, of the general formula:

in which R is (a) a linear or branched alkyl group which contains from 1 to 20 carbon atoms and is substituted by one to three groups (b) an alicyclic group which contains 4 to 20 carbon atoms and is optionally substituted by one to three groups (c) a carboxylate group which contains from 2 to 20 carbon atoms and is optionally substituted by a group $$-O-\underset{\underset{O}{\|}}{C}-O-CH_2-CH\underset{\diagdown\underset{\underset{\|}{C}}{O}\diagup}{-}CH_2,$$

(d) a polyoxyethylene of the formula $$R'+O-CH_2-CH_2\overline{\hspace{1pt}}_n,$$

in which n is between 1 and 40 and in which R' is a hydrocarbon group containing from 1 to 10 carbon atoms and optionally has one or two chains $-O-CH_2-CH_2-\overline{\hspace{1pt}}_{n'}$, in which n' is between 1 and 40, which chains are terminated by a group $$-O-\underset{\underset{O}{\|}}{C}-O-CH_2-CH\underset{\diagdown\underset{\underset{\|}{C}}{O}\diagup}{-}CH_2,$$

(e) a polyoxypropylene of the formula $$R''+O-CH_2-\underset{CH_3}{CH}\overline{\hspace{1pt}}_p$$

in which p is between 1 and 40 and in which R' is a hydrocarbon group containing from 1 to 10 carbon atoms and optionally carries one or two chains $$+O-CH_2-\underset{CH_3}{CH}\overline{\hspace{1pt}}_{p'},$$

in which p' is between 1 and 40, which chains are terminated by a group $$-O-\underset{\underset{O}{\|}}{C}-O-CH_2-CH\underset{\diagdown\underset{\underset{\|}{C}}{O}\diagup}{-}CH_2,$$

(f) an aryl group containing from 6 to 20 carbon atoms,
(g) a polyester of the formula $$R'''+O-\underset{\underset{O}{\|}}{C}-R_1-\underset{\underset{O}{\|}}{C}-O-R_2\overline{\hspace{1pt}}_Q$$

in which Q is between 1 and 20, in which $R_1$ and $R_2$ are identical or different and are a polymethylene chain having from 1 to 8 carbon atoms or a polyether chain having from 1 to 8 carbon atoms, and in which R' is a hydrocarbon group containing from 1 to 10 carbon atoms, or (h) an aliphatic polycarbonate $$\underset{\diagdown\underset{\underset{\|}{C}}{O}\diagup}{CH_2-CH}-CH_2-O-\underset{\underset{O}{\|}}{C}-O+R_3-O-\underset{\underset{O}{\|}}{C}-O-R_4-O-\underset{\underset{O}{\|}}{C}-O\overline{\hspace{1pt}}_r R_3-,$$

in which r is between 1 and 20 and in which $R_3$ and $R_4$ are identical or different, or in some cases identical and in other cases different, and are polymethylene groups containing from 2 to 8 carbon atoms or polyoxyethylene groups $$+CH_2-CH_2-O\overline{\hspace{1pt}}_t CH_2-CH_2-,$$

optionally in solution in an essentially water-immiscible organic solvent, so that the said valuable metal species are at least partially extracted into the organic phase;

(2) separating the charged organic phase containing the valuable metal species extracted from the aqueous solution in the form of a complex with said compound; and (3) recovering the valuable metal species from the organic phase by bringing the latter into contact with an aqueous stripping medium.

2. Process according to claim 1, wherein the valuable metal species treated is a member selected from the group consisting of Zn(II), Cd(II), Hg(II), Fe(III), Co(II), Cu(I), Cu(II), Rh(III), Pd(II), Pt(II), Mo(V), V(IV), Pb(II), Ag(I), Au(III), Ga(III), Na(I), K(I), Hg(I), U(IV), U(VI) and the lanthanides in oxidation states (II), (III) or (IV).

3. Process according to claim 1, wherein said compound is a member selected from the group consisting of alkyl 2,3-dioxycarbonylpropyl carbonates in which alkyl is methyl, n-propyl, n-butyl, n-pentyl, n-hexyl, n-heptyl, n-octyl and their higher linear homologues up to octadecyl, benzyl 2,3-dioxycarbonylpropyl carbonate, phenyl 2,3-dioxycarbonylpropyl carbonate, trimethylolpropane 2,3-dioxycarbonylpropyl carbonate, poly-[(diethylene glycol)carbonate]2,3-dioxycarbonylpropyl carbonates in which the polycarbonate part has a molecular weight of less than 3,000, poly-(butanediol carbonate)2,3-dioxycarbonylpropyl carbonates in which the polycarbonate part has a molecular weight of less than 2,000, poly-[(hexanediol/butanediol)carbonate]2,3-dioxycarbonylpropyl carbonates, the polyethylenes of the formula

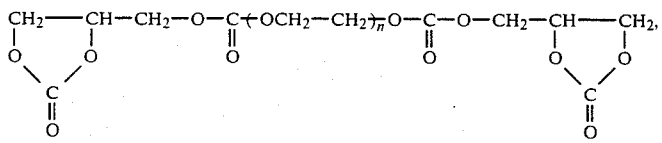

in which n is equal to or greater than 2 and of which the molecular weight preferably does not exceed 5,000, and the diol and triol 2,3-dioxycarbonylpropyl carbonates obtained by condensing propylene oxide with aliphatic diols or triols containing from 2 to 8 carbon atoms, and having an overall molecular weight of less than 3,000.

4. Process according to claim 1, wherein the pH of the aqueous phase charged with the valuable metal species to be extracted, and the pH of the stripping medium is between −1 and 12.

5. The process according to claim 1, wherein said organic phase is organic phase (d) which is a carbonate having cyclic carbonate groups and R is R′(OCH$_2$CH$_2$)$_n$, in which n is between 1 and 40 and in which R′ carries one or two chains $(\text{O}-\text{CH}_2-\text{CH}_2)_{n'}$, in which n′ is between 1 and 40, which chains are terminated by a group

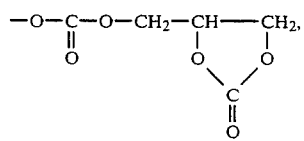

6. The process according to claim 5, wherein said compound is

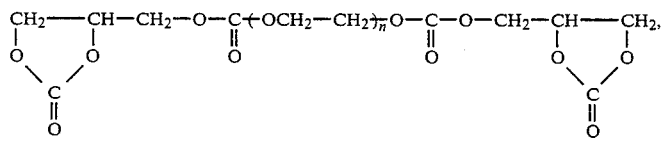

wherein n is equal to or greater than 2, and the molecular weight does not exceed 5000.

7. The process according to claim 6, wherein said compound is tetraethylene glycol di-(2,3-dioxycarbonylpropyl carbonate).

8. The process according to claim 5, 6 or 7, wherein the metal species is uranium.

9. The process according to claim 3 wherein in said poly-[(hexanediol/butanediol)carbonate]2,3-dioxycarbonylpropyl carbonate the polycarbonate part is in the form of a block copolymer.

* * * * *